(12) United States Patent
Kimmel et al.

(10) Patent No.: US 6,389,193 B1
(45) Date of Patent: May 14, 2002

(54) ROTATING HANDPIECE

(75) Inventors: Andrew I. Kimmel, Dana Point; Ioana M. Rizoiu, San Clemente, both of CA (US)

(73) Assignee: BioLase Technology, Inc., San Clemente, CA (US)

( * ) Notice: Subject to any disclaimer, the term of this patent is extended or adjusted under 35 U.S.C. 154(b) by 0 days.

(21) Appl. No.: 09/469,571

(22) Filed: Dec. 22, 1999

Related U.S. Application Data

(60) Provisional application No. 60/113,293, filed on Dec. 22, 1998.

(51) Int. Cl.⁷ ................................................. G02B 6/26
(52) U.S. Cl. .............................. 385/25; 385/31; 385/36
(58) Field of Search ............................... 385/15, 16, 18, 385/25, 26, 31, 36

(56) References Cited

U.S. PATENT DOCUMENTS

| | | | | |
|---|---|---|---|---|
| 4,109,998 A | * | 8/1978 | Iverson | 385/26 |
| 4,519,670 A | * | 5/1985 | Spinner et al. | 385/25 |
| 4,872,737 A | * | 10/1989 | Fukahori et al. | 385/25 |
| 5,204,922 A | * | 4/1993 | Weir et al. | 385/18 |
| 5,420,946 A | * | 5/1995 | Tsai | 385/26 X |

* cited by examiner

*Primary Examiner*—John D. Lee

(57) ABSTRACT

A rotating handpiece is disclosed, having a parabolic mirror coupling to optical fibers which are disposed perpendicularly to an input optical fiber and an output optical fiber. The output optical fiber of the two is adapted to rotate relative to a longitudinal axis of the input optical fiber.

15 Claims, 7 Drawing Sheets

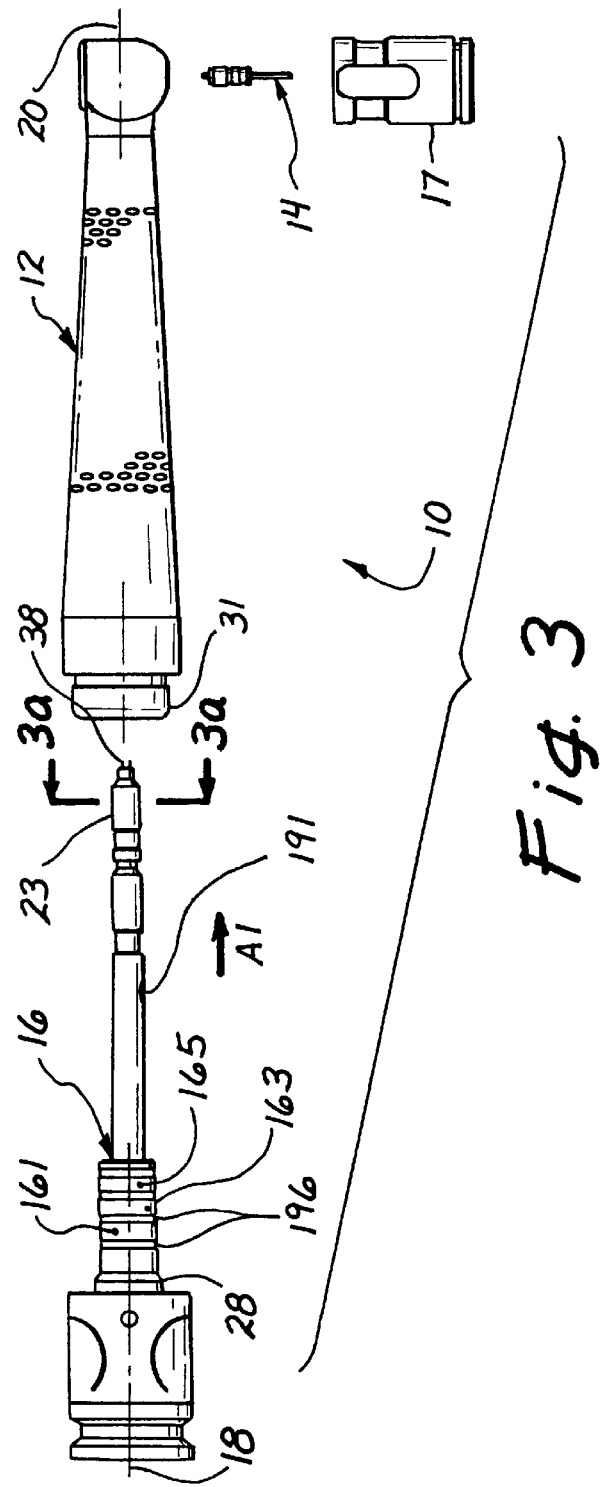
Fig. 3
Fig. 3a

ROTATING HANDPIECE

This application claims the benefit of U.S. provisional application Serial No. 60/113,293, which was filed on Dec. 22, 1998.

BACKGROUND OF THE INVENTION

1. Field of Invention

The present invention relates to hand pieces for delivering electromagnetic radiation.

2. Description of the Related Art

Hand pieces have existed in the prior art for delivering electromagnetic radiation.

SUMMARY OF THE INVENTION

The rotating hand piece of the present invention includes a removable fiber tip and a removable trunk fiber optic. The trunk fiber optic and the fiber tip are disposed perpendicularly, with a parabolic mirror disposed there between. Slight misalignments of the trunk fiber optics, as well as imperfections on the output surface of the fiber optic, are compensated by the parabolic mirror which consistently and efficiently focuses the electromagnetic energy into the input end of the fiber tip. Moreover, in accordance with one aspect of the present invention, the hand piece can be rotated about the longitudinal axis of the trunk fiber optic, with the parabolic mirror continuing to efficiently couple the electromagnetic energy from the trunk fiber optic into the fiber chip.

BRIEF DESCRIPTION OF THE DRAWINGS

FIG. 3 is a side elevation view of the rotating band piece and a partially disassembled state.

DETAILED DESCRIPTION OF THE PREFERRED EMBODIMENT

Figure 1:
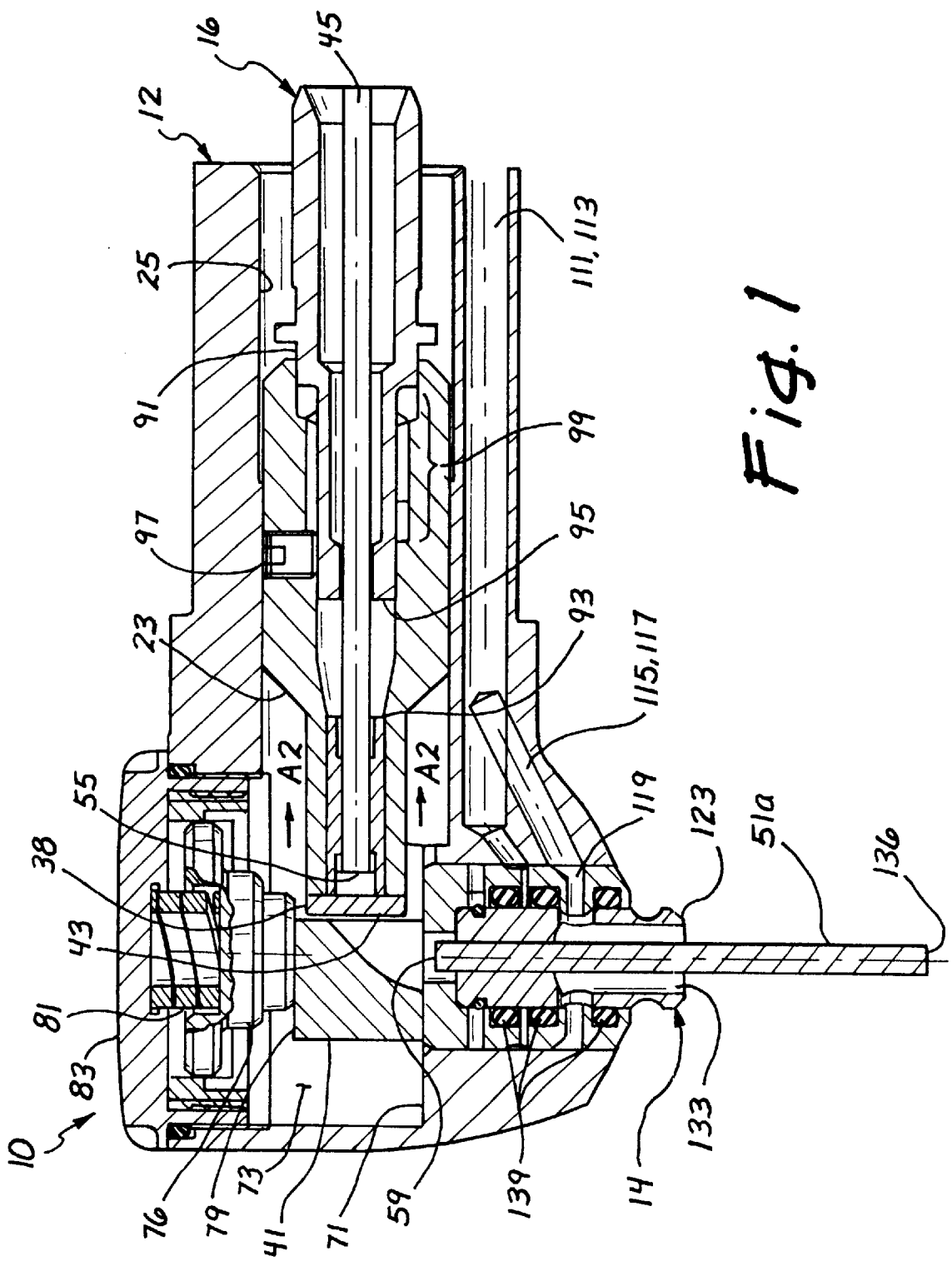
FIG. 1 is a cross sectional view of the rotating hand piece in accordance with the presently preferred embodiment.

Referring more particularly to the drawings, FIG. 1 illustrates a cross sectional view of the rotating hand piece 10. The rotating hand piece comprises a hand piece head 12, a removable fiber tip 14, and a removable trunk fiber assembly 16. These components can be seen in a partially disassembled state in FIG. 3, wherein the axis 18 of the removable trunk fiber assembly 16 is aligned with the axis 20 of the hand piece head 12 for insertion into the hand piece head 12. Once the axis 18 of the removable fiber assembly 16 is aligned with the axis 20 of the hand piece 12, the removable trunk fiber assembly 16 is moved in the direction of the arrow A1 into the hand piece head 12, while the axis 18 and 20 are maintained in approximate alignment. The contacting surface of the outer surface of the chuck 23 engages the inner surface 25 of the rotating hand piece 10, to thereby ensure alignment of the axis 18 of the removable trunk fiber assembly 16 and the axis 20 of the hand piece head 12. As the removable trunk fiber assembly 16 is inserted further in the direction A1 into the hand piece 12, the abutting surface 28 engages with a corresponding abutting surface (not shown) within the collar 31 of the hand piece head 12. The corresponding abutting surface 28 preferably snaps with the abutting surface 28, as the removable trunk fiber assembly 16 is fully inserted into the hand piece head 12. Any type of locking engagement between the abutting surface 28 and a corresponding abutting surface within the collar 31, as known in the art, may be used to ensure that the removable trunk fiber assembly 16 is always inserted the same distance into the hand piece head 12. As shown in FIG. 1, the distal tip 38 of the removable trunk fiber assembly 16 is brought into close proximity with the parabolic mirror 41. In the presently preferred embodiment, the distal tip 38 of the removable trunk fiber assembly 16 comprises a window 43 for protecting the trunk fiber optic 45 from contaminants, such as -water. In the alternative embodiment shown in FIG. 2, the distal tip 38a is not protected with a window. As shown in FIG. 1, the fiber tip 51 of the removable fiber ti 14 is also accurately placed in close proximity to the parabolic mirror 41. Electromagnetic energy exiting from the output rod 55 of the trunk fiber optic 45 is collected by the parabolic mirror 41 and, subsequently, reflected and focused onto the input end 59 of the fiber tip 51.

Figure 4A:
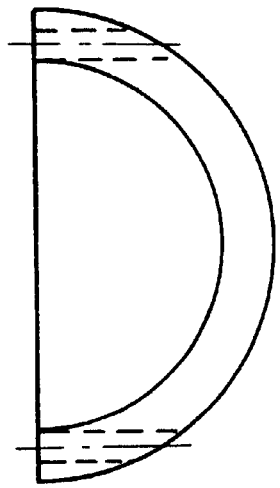
FIGS. 4–6 are other views of the invention.
Figure 4B:
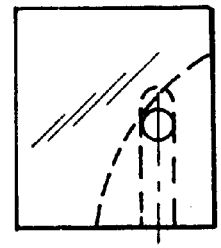
Figure 4C:
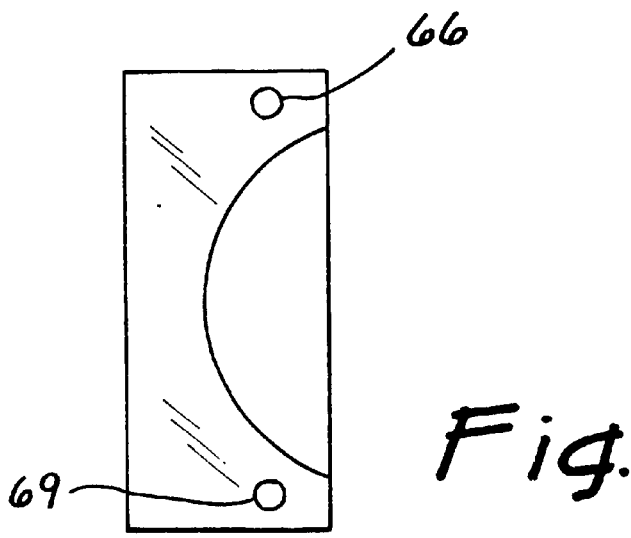

In the presently preferred embodiment, the electromagnetic energy exiting from the output end 55 of the trunk fiber optic 45 comprises a wavelength on the order of 3 $\mu$m. The material of the parabolic mirror 41 is selected to provide an efficient reflection and focusing into the input end 59. As presently embodied, the electromagnetic energy is generated from an Er:YSGG laser, and the material of the parabolic mirror 41 comprises a gold plating to provide reflectivity of approximately 99.9 percent. Other materials may be selected in accordance with design parameters. Other reflective surfaces and materials for the parabolic mirror 41 may be selected, in accordance with the laser being used and the desired efficiency of reflection. For example, if a lower reflectivity is selected, then additional cooling may be needed for the parabolic mirror 41 (such as a greater flow rate of cooled and/or filtered air across the surface of the parabolic mirror 41). FIGS. 4a, 4b and 4c illustrate various views of the parabolic mirrors 41 of the presently preferred embodiment. The flat surface of the parabolic mirror 41, which is closest to the fiber tip 51, is preferably provided with two recessed areas 66 and 69. These two recessed areas mate with corresponding protrusions (not shown) on the floor 71 of the internal chamber 73 of the handpiece head 12. A spring loaded plunger 76 presses against the upper surface 79 of the parabolic mirror 41 under the pressure of the spring 81. A screw cap 83 holds the spring 81 against the spring loaded plunger 76. The combination of the spring loaded plunger 76, the recessed areas 66,69 of the parabolic minor 41, and the corresponding protrusions on the pressure of the spring 81. A screw cap 83 holds the spring 81 against the spring loaded plunger 76. The combination of the spring loaded plunger 76, the recessed areas 66, 69 of the parabolic minor 41, and the corresponding protrusions on the floor 71, together, accurately align the parabolic mirror 41 for efficient coupling of electromagnetic energy between the output end 55 of the trunk fiber optic 45 and the input end 59 of the fiber tip 51. In modified embodiments, either or both of the output end 55 of the trunk fiber optic 45 and the input end 59 of the fiber tip 51 is/or provided with an anti-reflective coating. Although it is preferred to have the trunk fiber optic 45 perfectly aligned in relation to the parabolic 41 and the fiber tip 51, the alignment between these three elements is seldomly perfect. In the presently preferred embodiment, the misalignment of the axis of the trunk fiber optic 45 and the axis of the fiber tip 51 is within plus or minus 1 percent error.

Figure 2:
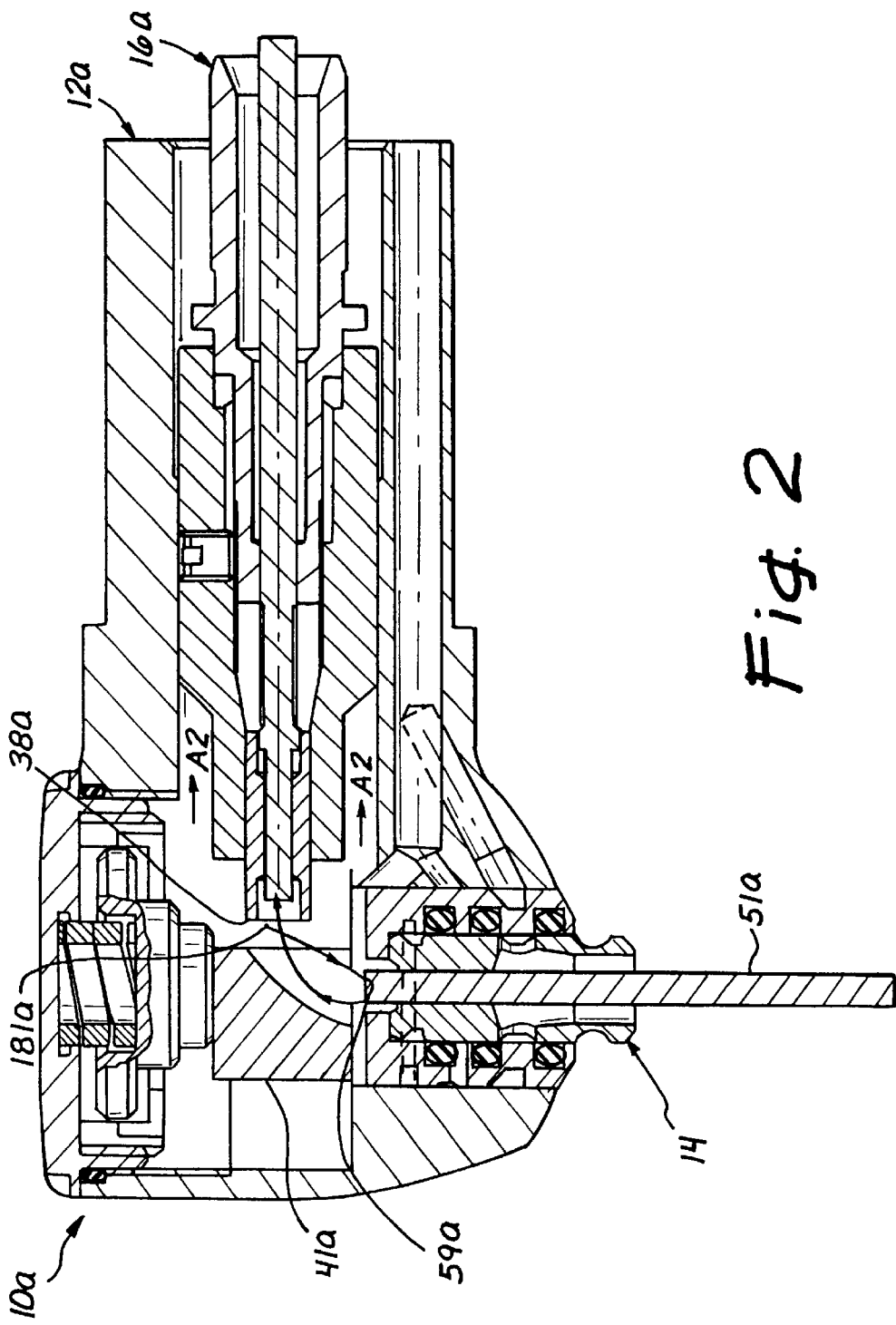
FIGS. 2 and 2a are cross sectional views of two alternative embodiments of the rotating hand piece.
Figure 2A:
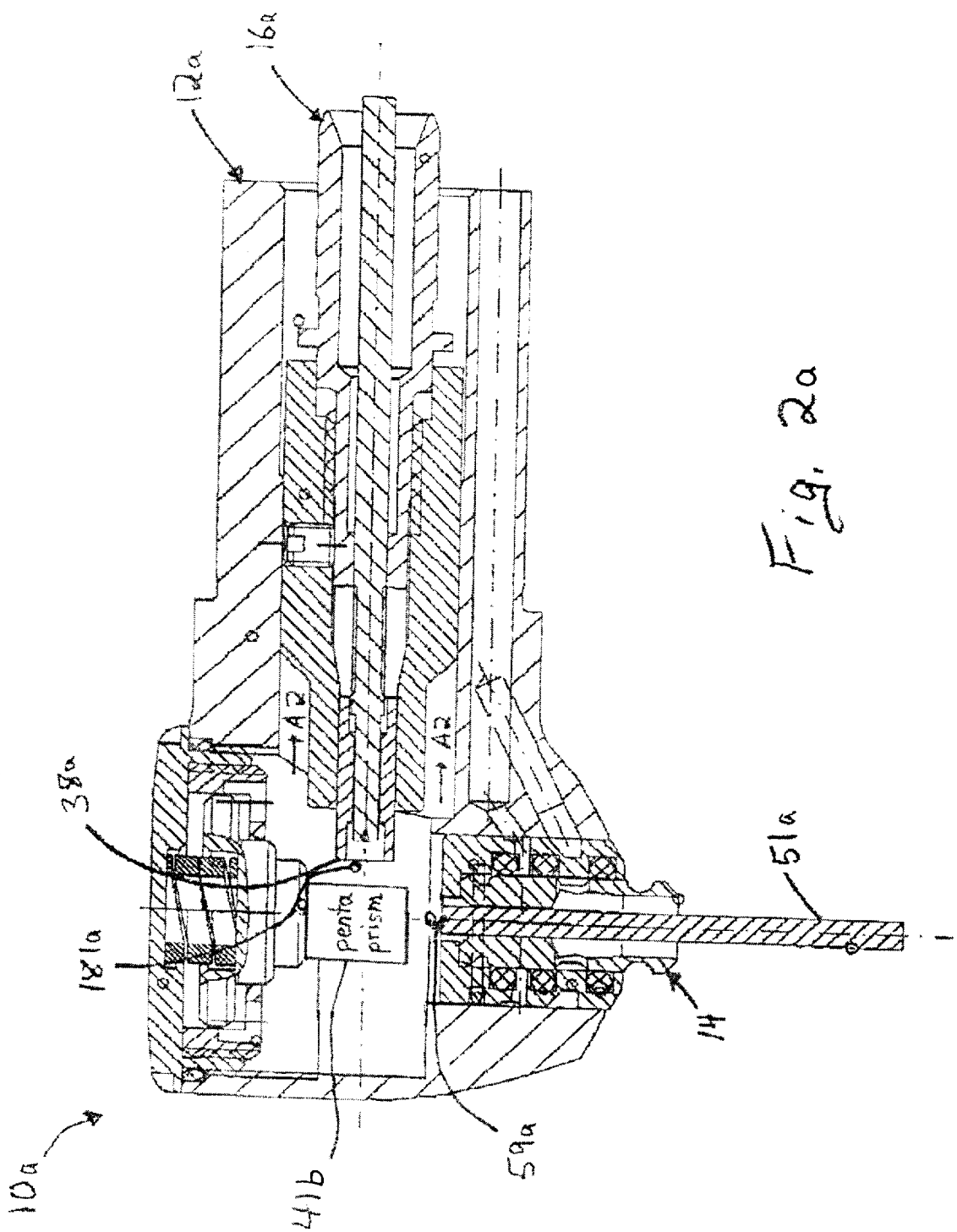

In a modified embodiment, as shown in FIG. 2a, a pentaprism (five-sided prism) 41b is used instead of the parabolic mirror 41 for coupling the trunk fiber optic 45 to the fiber tip 51.

In addition to slight misalignment of the axis of the trunk fiber optic 45, slight imperfections on the output end 55 of the trunk fiber optic 45 may also be present. The parabolic mirror 41 corrects for both of these slight errors, by collecting the electromagnetic energy from the output end 55 of the front fiber optic 45 and, subsequently, focusing the electromagnetic energy into the input end 55 of the fiber tip 51.

The parabolic mirror 41 may also comprise molypdium, in a preferred embodiment.

The clamp assembly 91 operates to firmly grip and hold the trunk fiber optic 45. In the presently preferred embodiment, the clamp assembly 91 is provided with at least one slit, which extends from the distal end 93 of the clamp assembly 91 to a region 95 just distal of the set screw 97. As presently embodied, the at least one slit extending from the distal end 93 to the region 95 just distal of the set screw 97 comprises two slits, which are adapted to allow the clamp assembly 91 to be compressed by the chuck 23 onto the trunk fiber optic 45. The chuck 23 thus the at least one slit extending from the distal end 93 to the region 95 just distal of the set screw 97 comprises two slits, which are adapted to allow the clamp assembly 91 to be compressed by the chuck 23 onto the trunk fiber optic 45. The chuck 23 thus presses against the portion of the clamp assembly 91, wherein the portion is defined between the distal end 93 and the region 95, to thereby have the clamp assembly 91 squeeze and hold the trunk fiber optic 45 in place. In the presently preferred embodiment, the set screw 97 is used lo hold the chuck 23 in place and prevent rotation thereof. In the illustrated embodiment, the outer surface of the clamp assembly 91 is provided with threads 99 for engaging with corresponding threads on the inner surface of the chuck 23. In the presently preferred embodiment, the chuck 23 is screwed onto the threads of the clamp assembly 91, before the removable trunk fiber assembly 16 is inserted into the handpiece 12. The chuck 23 is screwed onto the clamp assembly 91 to a predetermed tightness, and then the set screw 97 is secured thereto to securely hold the chuck 23 to the clamp assembly 91. Subsequently, the removable trunk fiber assembly 16 is inserted and secured into the handpiece head 12.

Figure 5A:
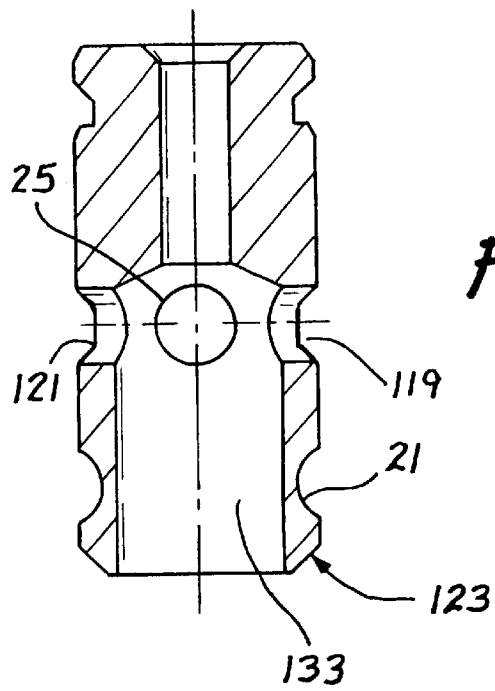
Figure 5B:
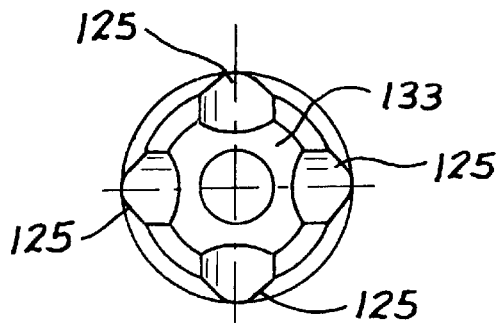
Figure 5C:
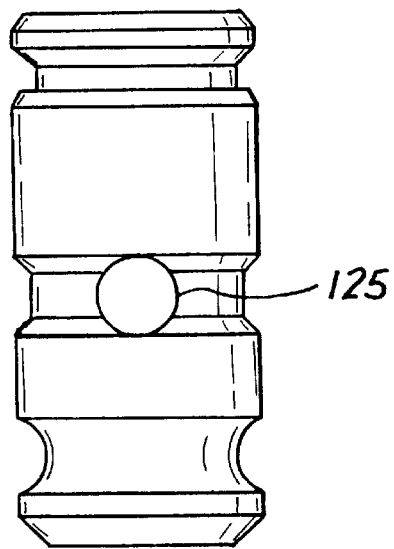

The rotating handpiece 10 of the presently preferred embodiment uses the electromagnetically induced cutting system disclosed in U.S. Pat. No. 5,741,247, the entire contents of which are expressly incorporated herein by reference. In the illustrated embodiment of FIG 1, separate fair and fluid lines 111,113 run parallel to one another in the distal direction toward the feed channels 115,117. The feed channels 115, 117, carrying a supply of air and water, respectively, feed into a circumferential chamber 119. Referring to figures 5a–5c, the circumferential chamber 119 is formed in the fiber tip ferrule 121 is formed in a tapered section 121 of the fiber tip ferrule 123. As can be seen from FIG. 5b, for example, four orifices 125 are disposed in the tapered section 121 of the fiber chip ferrule 123. Air traveling to the circumferential chamber 119 from the feed channel 115, and water traveling into the circumferential chamber 119 from the feed channel 117, are both initially mixed in the circumferential chamber 119. Subsequently, the initially-mixed air travels through the circumferential chamber 119 and enters through the orifices 125. The air and water is further mixed and atomized within the internal chamber 133. The atomized water under air pressure subsequently travels along the fiber chip 51 in a direction toward the output end 136 of the fiber tip 51. In the presently preferred embodiment, three o-ring seals 139 are provided to seal the inside of the rotating handpiece from the air and water.

Figure 6A:
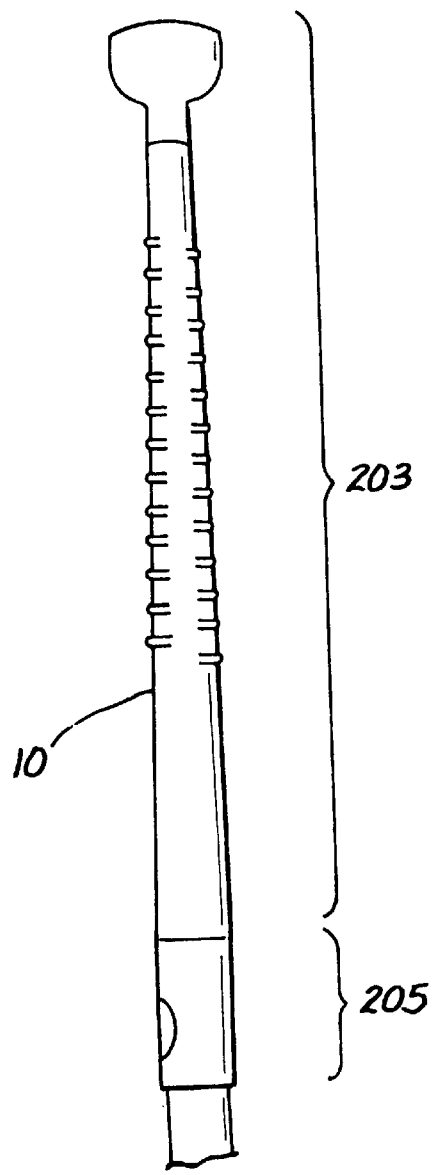
Figure 6B:
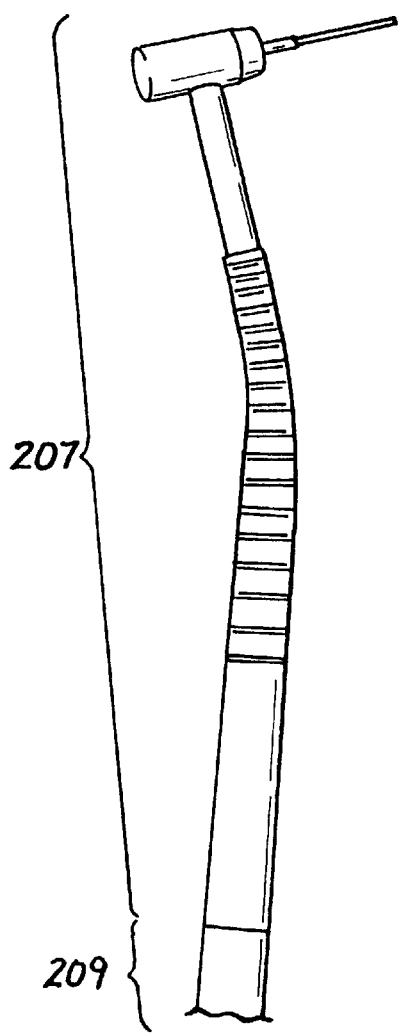

Referring to FIG. 3, the removable trunk fiber assembly 16 is preferably provided with three radial ports for introducing air, water, and (optionally) cooling air. More particularly, a fluid radial channel 161 feeds fluid (e.g., water) into the fluid channel 111, an air radial channel 163 feeds air into the air channel 113, and an optional cooling-air radial channel 165 feeds cooling air along a cooling-air channel, which exits in close proximity to the parabolic mirror 41. In a preferred embodiment, the exit angle of the cooling air channel directs cooling air directly onto the parabolic mirror 41, so that the cooling air is reflected from the parabolic mirror 41 onto the input end 59 of the fiber tip 51 and, subsequently, onto the window 43. In FIG. 2, the cooling air exits from an orifice 181a and is channeled directly onto the input end 59a of the fiber tip 51a. Subsequently, the air is directed onto the parabolic mirror 41 and reflected onto the output end 55 of the trunk fiber optic 45. This configuration could also be implemented for the system of FIG. 1, wherein the cooling air subsequently is directed onto the window 43. Alternatively, in the embodiment of FIG. 2, the cooling air exiting the orifice 181a can be channeled directly onto the parabolic mirror 41, focusing onto the input end 59a of the fiber tip 51. In the embodiments of both FIG. 1 and FIG. 1, the cooling air is subsequently channeled in the direction of the arrows A2 through channels formed in the chuck 23. As shown in FIG. 3a, the chuck 23 preferably has portions of its two sides removed, to thereby form channels for passage of the cooling air. The cooling air travels through the channels of the chuck 23 under a vacuum pressure and, subsequently, is drawn into a removal port 191. Upon entering the removal port 191 under the vacuum, the cooling air travels in a direction opposite to the arrow A1 and exits the removal trunk fiber assembly 16. The four 0-rings 196 insulate the radial channels 161,163, 165 from one another. FIG. 6a illustrates a side elevation view of the assembled rotating handpiece 10 and FIG. 6b illustrates a modified embodiment of the rotating handpiece 10, wherein the neck is slightly bent. In FIGS. 6a the portion indicated by reference numeral 203 is adapted to rotate about an axis of the rotating handpiece 10. The portion 205 does not rotate. Similarly, in FIG. 6b, the portion 207 is adapted to rotate about an axis of the rotating handpiece, and the portion 209 docs not rotate. In the embodiment of FIG. 6b, the trunk fiber optic is configured to be slightly flexible, since the trunk fiber optic will need to bend and flex as the portion 207 is rotated relative to the portion 209. In either of the embodiments of FIGS. 6a and 6b, the user holds the rotating portion (203 or 207) with his or her thumb and two fingers (such as is conventional in the art) and allows the stationary portion (205 or 209) to rest on a portion of the hand bridging the user's forefinger and thumb. The three fingers holding the rotating portion (203 or 207) contact the rotating portion and can rotate the rotating portion, as the fixed portion (205 or 209) does not rotate and rests on the portion of the hand bridging the hand and the forefinger.

What is claimed is:

1. A medical rotating handpiece for performing medical procedures on tissue comprising:

a trunk fiber optic coupled to the medical rotating handpiece and having an output end for delivering electromagnetic energy therefrom;

a fiber tip coupled to the medical rotating handpiece and having an input end for receiving electro-magnetic energy and an output end for outputting electromagnetic energy, and a parabolic mirror disposed within the medical rotating handpiece between the output end of the trunk fiber optic and the input end of the fiber tip.

2. The medical rotating handpiece as set forth in claim 1, wherein the parabolic mirror is positioned to receive electromagnetic energy from the output end of the trunk fiber optic and to focus the received electromagnetic energy into the input end of the fiber tip.

3. The medical rotating handpiece as set forth in claim 1, wherein a longitudinal axis of the trunk fiber optic is perpendicularly disposed relative to the longitudinal axis of the fiber tip.

4. The medical rotating handpiece as set forth in claim 1, wherein the fiber tip is adapted to rotate about the longitudinal axis of the trunk fiber optic.

5. The medical rotating handpiece as set forth in claim 1, wherein the fiber tip is adapted to rotate in a plane, wherein the plane is perpendicular to the longitudinal axis of the trunk fiber optic.

6. A rotating handpiece comprising:
   a trunk fiber optic having an output end for delivering electromagnetic energy therefrom;
   a fiber tip having an input end for receiving electromagnetic energy and an output end for outputting electromagnetic energy; and
   a pentaprism disposed between the output end of the trunk fiber optic and the input end of the fiber tip.

7. The rotating handpiece as set forth in claim 6, wherein the pentaprism is positioned to receive electromagnetic energy from the output end of the trunk fiber optic and to focus the received electromagnetic energy into the input end of the fiber tip.

8. The rotating handpiece as set forth in claim 6, wherein a longitudinal axis of the trunk fiber optic is perpendicularly disposed relative to the longitudinal axis of the fiber tip.

9. The rotaing handpiece as set forth in claim 6, wherein the fiber tip is adapted to rotate about the longitudinal axis of the trunk fiber optic.

10. The rotating handpiece as set forth in claim 6, wherein the fiber tip is adapted to rotate in a plane, wherein the plane is perpendicular to the longitudinal axis of the trunk fiber optic.

11. An industrial rotating handpiece for performing cutting or ablating procedures on industrial materials comprising:
   a trunk fiber optic coupled to the industrial rotating handpiece and having an output end for delivering electromagnetic energy therefrom;
   a fiber tip coupled to the industrial rotating handpiece and having an input end for receiving electro-magnetic energy and an output end for outputting electromagnetic energy, and
   a parabolic mirror disposed within the industrial rotating handpiece between the output end of the trunk fiber optic and the input end of the fiber tip.

12. The industrial rotating handpiece as set forth in claim 11, wherein the parabolic mirror is positioned to receive electromagnetic energy from the output end of the trunk fiber optic and to focus the received electromagnetic energy into the input end of the fiber tip.

13. The industrial rotating handpiece as set forth in claim 11, wherein a longitudinal axis of the trunk fiber optic is perpendicularly disposed relative to the longitudinal axis of the fiber tip.

14. The industrial rotating handpiece as set forth in claim 11, wherein the fiber tip is adapted to rotate about the longitudinal axis of the trunk fiber optic.

15. The industrial rotating handpiece as set forth in claim 11, wherein the fiber tip is adapted to rotate in a plane, wherein the plane is perpendicular to the longitudinal axis of the trunk fiber optic.

\* \* \* \* \*

UNITED STATES PATENT AND TRADEMARK OFFICE
CERTIFICATE OF CORRECTION

PATENT NO.     : 6,389,193 B1
DATED          : May 14, 2002
INVENTOR(S)    : Kimmel et al.

It is certified that error appears in the above-identified patent and that said Letters Patent is hereby corrected as shown below:

<u>Title page,</u>
Item [74], should read -- *Attorney, Agent, or Firm*-Stout, Uxa, Buyan & Mullins, LLP --

<u>Column 2,</u>
Line 14, "fiber ti 14" should read -- fiber tip 14 --.
Line 52, "minor 41" should read -- mirror 41 --.
Line 58, "51 is/or provided" should read -- 51 is/are provided --.
Line 60, "parabolic 41" should read -- parabolic mirror 41 --.

<u>Column 3,</u>
Line 8, "comprise molypdium," should read -- comprise molybdenum, --.
Line 28, "is used lo" should read -- is used to --.
Line 47, "fair and fluid" should read -- air and fluid --.

<u>Column 4,</u>
Line 63, "receiving electro-magnetic" should read -- receiving electromagnetic --.

<u>Column 6,</u>
Line 12, "receiving electro-magnetic" should read -- receiving electromagnetic --.

Signed and Sealed this

Sixth Day of August, 2002

*Attest:*

*Attesting Officer*

JAMES E. ROGAN
*Director of the United States Patent and Trademark Office*